(12) United States Patent
Van Amsterdam

(10) Patent No.: US 7,709,463 B2
(45) Date of Patent: May 4, 2010

(54) IDRAPARINUX (SANORG34006) FOR TREATMENT OF VENOUS EVENTS IN PATIENTS WITH DEEP VENOUS THROMBOSIS

(75) Inventor: Ronald Gijsbertus Maria Van Amsterdam, Oss (NL)

(73) Assignee: Sanofi-Aventis, Paris (FR)

( * ) Notice: Subject to any disclaimer, the term of this patent is extended or adjusted under 35 U.S.C. 154(b) by 1197 days.

(21) Appl. No.: 10/502,706

(22) PCT Filed: Jan. 23, 2003

(86) PCT No.: PCT/EP03/00696

§ 371 (c)(1),
(2), (4) Date: Feb. 15, 2005

(87) PCT Pub. No.: WO03/063881

PCT Pub. Date: Aug. 7, 2003

(65) Prior Publication Data

US 2005/0209175 A1    Sep. 22, 2005

(30) Foreign Application Priority Data

Jan. 29, 2002   (EP)   ................................ 002075374

(51) Int. Cl.
*A61K 31/715*   (2006.01)
*A61K 31/737*   (2006.01)
*A61K 31/7028*  (2006.01)
*A61K 31/70*    (2006.01)

(52) U.S. Cl. ............................. 514/54; 514/23; 514/25; 536/123.1; 536/122

(58) Field of Classification Search ................... 514/54, 514/23, 25; 536/123.1, 122
See application file for complete search history.

(56) References Cited

U.S. PATENT DOCUMENTS 5,378,829 A * 1/1995 Petitou et al. ............... 536/118

OTHER PUBLICATIONS

Sanjoy, et al., Synthesis of Conformationally Locked L-Iduronic Acid Derivatives: Direct Evidence for a Critical Role of the Skew-Boat S0 Conformer in the Activation of Antithrombin by Heparin, Chem. Eur. J. 2001; 7, No. 22; pp. 4821-4834.
Walenga, et al., Biochemical and Pharmacological Rationale for the Development of a Synthetic Heparin Pentasaccharide, Thrombosis Research; 1997; 86(1); pp. 1-36.

* cited by examiner

*Primary Examiner*—Shaojia Anna Jiang
*Assistant Examiner*—Michael C Henry
(74) *Attorney, Agent, or Firm*—Ronald G. Ort; James W. Bolcsak

(57) ABSTRACT

The invention relates to a dose of 2.5 mg of the pentasaccharide methyl O-(2,3,4-tri-O-methyl-6-O-sulfo-α-D-glucopyranosyl)-(1→4)-O-(2,3-di-O-methyl-β-D-glucopyranosyl uronic acid)-(1→4)-O-(2,3,6-tri-O-sulfo-α-D-glucopyranosyl)-(1→4)-O-(2,3-di-O-methyl-α-L-idopyranosyl uronic acid)-(1→4)-2,3,6-tri-O-sulfo-α-D-glucopyranoside or a pharmaceutically acceptable salt thereof for use in therapy, in particular for the treatment of venous thromboembolic events in patients with deep venous thrombosis.

2 Claims, 1 Drawing Sheet

IDRAPARINUX (SANORG34006) FOR TREATMENT OF VENOUS EVENTS IN PATIENTS WITH DEEP VENOUS THROMBOSIS

The invention relates to a specific dose of SanOrg 34006 for use in the treatment and secondary prophylaxis of venous thromboembolic events (VTE) in patients with deep venous thrombosis (DVT).

Recurrence of VTE after treatment of acute DVT is a common clinical feature after the acute treatment of the disease with antithrombotic therapy has been completed. Therefore, to decrease the long-term recurrence rates long-term antithrombotic therapy is required. Usually, unfractionated heparin (UFH), low-molecular-weight heparin (LMWH, thrombolytic agents, and warfarin are used to treat VTE. The currently accepted approach of acute treatment of DVT followed by long-term therapy is to begin heparin and oral anticoagulant therapy (wafarin or another coumarin) together at the time of diagnosis and to discontinue the heparin therapy between the fourth and seventh day. Several randomized trials in patients with VTE have shown that 5 to 7 days of initial heparin therapy coupled with early warfarin initiation and treatment for at least 3 months is effective and safe [Hyers, et al., ACCP 2001, CHEST 2001; 119:180S]. For effective treatment, both animal and human studies have shown that a plasma heparin level in the range of 0.2-0.4 IU/mL inhibits thrombus propagation [Hyers, et al., ACCP 2001, CHEST 2001; 119:178S].

Surprisingly and contrary to common practice in the art, it has now been found that a dose of as low as of 2.5 mg of the pentasaccharide methyl O-(2,3,4-tri-O-methyl-6-O-sulfo-α-D-glucopyranosyl)-(1→4)-O-(2,3-di-O-methyl-β-D-glucopyranosyl uronic acid)-(1→4)-O-(2,3,6-tri-O-sulfo-α-D-glucopyranosyl)-(1→4)-O-(2,3-di-O-methyl-α-L-idopyranosyl uronic acid)-(1→4)-2,3,6-tri-O-sulfo-α-D-glucopyranoside or a pharmaceutically acceptable salt thereof (in particular its nonasodium salt SanOrg34006, see e.g. U.S. Pat. No. 5,378,829) is effective and safe for the treatment and secondary prophylaxis of VTE in patients with DVT when administered once a week. After administration of the dose of 2.5 mg of SanOrg34006 the plasma trough levels ($C_{min}$=126±63 ng/mL) correspond with 0.09-0.26 anti-Xa U/mL, whereas 0.2-0.4 IU/mL UFH plus additional anti-IIa activity is generally considered effective in VTE-treatment (vide supra).

Since therapeutic regimens for the treatment and secondary prophylaxis of VTE in patients with DVT may be associated with increased bleeding risk, the lowest dose of an anticoagulant which is effective and safe is the most preferred dose. The once-a-week administration of the low dose of SanOrg34006 according to the present invention results in very low plasia levels which unexpectedly are still effective in the prophylaxis and treatment of VTE.

The therapeutic regimen of the present invention does not require subsequent monitoring and dose adjustment.

The term "pharmaceutically acceptable salt" means a salt with counter-ions like alkali or earth-alkali metal ions, like sodium, calcium, or magnesium.

The dose of the pentasaccharide of this invention is administered as a subcutaneous injection to the patient undergoing treatment. Preferably, the patient is a human.

The pentasaccharide may be used as a pharmaceutical composition comprising said pentasaccharide together with pharmaceutically acceptable auxiliaries and optionally other therapeutic agents. The term "acceptable" means being compatible with the other ingredients of the composition and not deleterious to the recipients thereof.

The pharmaceutical composition for parenteral administration of the dose of the pentasaccharide of this invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries and liquids, e.g. as described in the standard reference, Gennaro et al., Remington's Pharmaceutical Sciences, (18th ed., Mack Publishing Company, 1990, see especially Part 8: Pharmaceutical Preparations and Their Manufacture), the pentasaccharide can be applied as a fluid composition, an injection preparation, in the form of a solution, suspension or emulsion. Aqueous suspensions, isotonic saline solutions and sterile injectable solutions may be used, containing pharmaceutically acceptable dispersing agents and/or wetting agents, such as propylene glycol or butylene glycol. The preferred pharmaceutical composition is an isotonic saline solution of the pentasaccharide. The pharmaceutical composition according to the invention may also be presented in the form of a veterinary composition, such compositions may be prepared by methods conventional in the art.

The invention is further illustrated by the following example.

EXAMPLE

Clinical data demonstrating both efficacy and safety of the (use of the) dose of 2.5 mg of SanOrg34006 in the treatment and secondary prophylaxis of venous thromboembolic events (VTE) in patients with deep venous thrombosis (DVT) when compared to warfarin.

Overall Study Design

Figure 1:
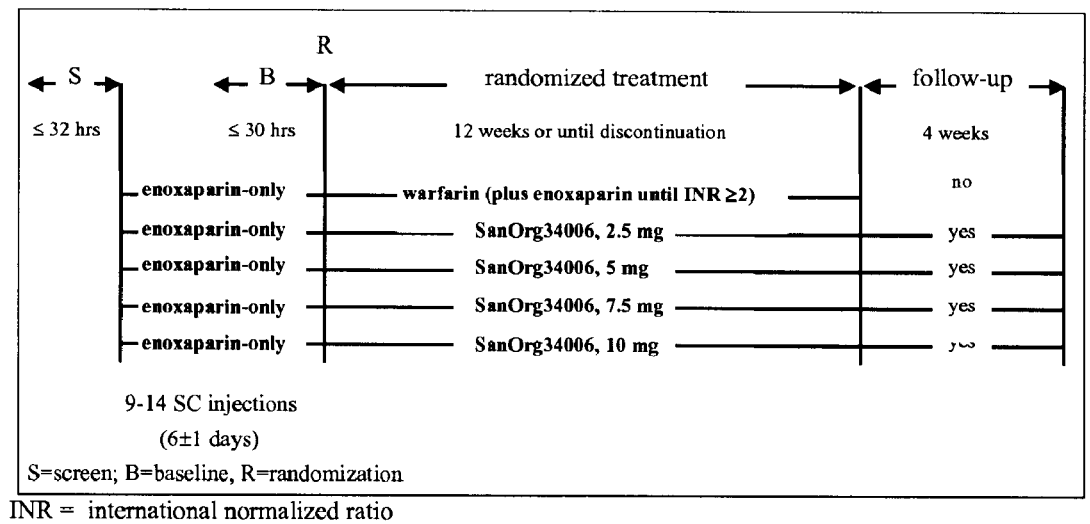
FIG. 1 is a table setting forth the study design of the Example.

The study was a phase II, multicenter, randomized study in five parallel groups, double blind for the dose of SanOrg34006, and open label, assessor blind for oral warfarin (comparator group). The study design is illustrated in FIG. 1.

After an initial treatment of 9-14 injections (corresponding to 6±1 days) with enoxaparin (representing the LMWHs) for all patients, a total of 650 patients with confirmed symptomatic proximal DVT were to be randomly assigned to one of the treatment groups (2.5 mg, 5 mg, 7.5 mg, or 10 mg SC San- Org34006, or oral warfarin). Each treatment group was to consist of 130 patients, of which at least 100 patients eligible for inclusion in the Intent-To-Treat (ITT) group. Subjects in the SanOrg34006 treatment groups were to be followed-up during a four-week period after the final assessments.

Objectives

The primary (interrelated) objectives of this study were:
to assess the dose-effect relationship of SanOrg34006 to prevent the recurrence and extension of VTE after a period of initial treatment of symptomatic proximal DVT with enoxaparin;
to determine the optimum dose of SanOrg34006 which will be used in further comparative therapeutic studies. This optimum dose was selected considering efficacy, safety, coagulation markers and overall performance.

The secondary objective was to assess population pharmacokinetics of SanOrg34006.

Diagnosis and Criteria for Inclusion:
symptomatic proximal DVT (defined as thrombosis in the Popliteal vein, the Superficial Femoral vein or the Common Femoral vein) confirmed by CUS (Compression Ultra Sound/echo) or venography,
males or non-pregnant females;
signed written informed consent.

Duration of Treatment:
9-14 Enoxaparin injections per patient (corresponding with 5-7 days of treatment), followed by 12 once-weekly administrations of SanOrg34006 or a 12-week course of Warfarin.

Duration of Study Participation:
6±1 Day enoxaparin treatment and up to 12 Weeks±1 Day of randomized treatment, and for the SanOrg34006 treatment groups an additional follow-up of 4 weeks.

Criteria for Evaluation:
Efficacy
Primary efficacy parameter: change in thrombotic burden as assessed by the central adjudication committee using a 3-point ordinal outcome scale for the comparison of CUS and PLS (Perfusion Lung Scan) after 12 weeks of randomized treatment with baseline measurements (i.e. deterioration, normalization, or no relevant change) including a supplementary analysis on substantial improvement.

Secondary efficacy parameters: change in thrombotic burden using a binary scale (i.e. deterioration versus no deterioration); change of CUS on a 3-point ordinal scale; change of PLS on a 3-point ordinal scale; the composite clinical outcome (non-fatal symptomatic PE and/or recurrent DVT, death due to PE and/or DVT or unexplained, and any important change in therapeutic management of thrombotic events); coagulation markers: plasma D-dimer (fibrin fragment, released in process of thrombolysis; measure for ongoing thrombosis) and TAT (Thrombin-Antithrombin Complex) concentrations during the study treatment.

Safety
Primary safety parameters: incidence of major bleeding and decreased platelet count.
Secondary efficacy parameters: (serious) adverse events, laboratory parameters (hematology, biochemistry, coagulation status, platelet counts), and vital signs (blood pressure, heart rate, body weight).

Pharmacokinetics
Plasma concentrations of SanOrg34006 were assessed within 48 h prior to the administration of SanOrg34006 in Weeks 2, 4 and 7. In addition during Week 7 within the time frames 0.5-2 h, 2-6 h, 6-48 h and 120-168 h post dose. In a subset of patients a more extensive sampling scheme was applied with pre-dose samples before each administration and the serial scheme for Week 7 also applied to Week 1 and 12. The parameters $C_{max}$, $C_{min}$ and $AUC_{(0-168)}$ were calculated from the more extensive data in Week 7 (and Week 1 and 12 for the aforementioned subset).

Primary Efficacy Analysis

TABLE 1

Summary of Overall Changes in Thrombotic Burden Assessed by CAC (3-point Scale); Intent to Treat Group. Data include unexplained deaths, symptomatic events (within deterioration), (lack of) compression ultrasonographical changes in the upper leg and (lack of) scintigraphic changes in the lungs.

| | SanOrg34006 | | | | |
|---|---|---|---|---|---|
| Outcome | 2.5 mg (N = 125) n (%) | 5 mg (N = 128) n (%) | 7.5 mg (N = 118) n (%) | 10 mg (N = 119) n (%) | Warfarin (N = 124) n (%) |
| Normalization | 32 (25.6) | 31 (24.2) | 29 (24.6) | 30 (25.2) | 31 (25.0) |
| No Relevant Change | 87 (69.6) | 89 (69.5) | 81 (68.6) | 74 (62.2) | 84 (67.7) |
| Deterioration | 6 (4.8) | 8 (6.3) | 8 (6.8) | 15 (12.6) | 9 (7.3) |
| Pairwise Comparison[a] | 0.936 | 0.906 | 0.984 | 0.360 | |

Percentages are based on evaluable scores. CAC = Central Adjudication Committee
[a]P values for comparison with warfarin, based on CMH test, stratifying for active cancer.

The P-value for Dose Trend is p=0.388 for SanOrg34006, based on the Cochran-Mantel-Haenszel (non-zero correlation) test for trends across dosage (CMH test), stratifying for active cancer.

Secondary Efficacy Analyses

TABLE 2

Summary of Composite Clinical Outcome Assessed by CAC; Intent to Treat Group

| Fatal or non-fatal Recurrent DVT, Symptomatic PE or Unexplained Death[a] | | SanOrg34006 | | | | |
|---|---|---|---|---|---|---|
| | | 2.5 mg (N = 125) | 5 mg (N = 128) | 7.5 mg (N = 118) | 10 mg (N = 119) | Warfarin (N = 124) |
| No | n (%) | 125 (100.0) | 126 (98.4) | 118 (100.0) | 116 (97.5) | 122 (98.4) |
| | 95% CI | [97.1, 100] | [94.5, 99.8] | [96.9, 100] | [92.8, 99.5] | [94.3, 99.8] |
| Yes | n (%) | 0 (0.0) | 2 (1.6) | 0 (0.0) | 3 (2.5) | 2 (1.6) |
| | 95% CI | [0.0, 2.9] | [0.2, 5.5] | [0.0, 3.1] | [0.5, 7.2] | [0.2, 5.7] |

CI = Confidence Interval

TABLE 3

Summary of Overall Changes in Thrombotic Burden Assessed by CAC (2-point Scale); Intent to Treat Group

|  |  | SanOrg34006 | | | | Warfarin |
|---|---|---|---|---|---|---|
|  |  | 2.5 mg (N = 125) | 5 mg (N = 128) | 7.5 mg (N = 118) | 10 mg (N = 119) | (N = 124) |
| No | n (%) | 119 (95.2) | 120 (93.8) | 110 (93.2) | 104 (87.4) | 115 (92.7) |
| Deterioration | 95% CI | [89.8, 98.2] | [88.1, 97.3] | [87.1, 97.0] | [80.1, 92.8] | [6.7, 96.6] |
| Deterioration | n (%) | 6 (4.8) | 8 (6.3) | 8 (6.8) | 15 (12.6) | 9 (7.3) |
|  | 95% CI | [1.8, 10.2] | [2.7, 11.9] | [3.0, 12.9] | [7.2, 19.9] | [3.4, 13.3] |
| Pairwise comparison[a] |  | 0.570 | 0.550 | 0.655 | 0.219 |  |

[a]P-values for comparison with warfarin, based on CMH test, stratifying for active cancer.

The P-value for Dose Trend is p=0.062 for SanOrg34006, based on CMH (non-zero correlation) test, stratifying for active cancer.

Bleeding Assessments and Related Criteria

TABLE 4

Analysis of Major Bleeding Events During Randomized Treatment; All Patients With Randomized Treatment group

|  | SanOrg34006 | | | | Warfarin |
|---|---|---|---|---|---|
|  | 2.5 mg (N = 131) | 5 mg (N = 135) | 7.5 mg (N = 130) | 10 mg (N = 131) | (N = 132) |
| Outcome | n (%) | n (%) | n (%) | n (%) | n (%) |
| Major Bleeding | 0 (0.0) | 4 (3.0) | 2 (1.5) | 9 (6.9) | 1 (0.8) |
| No Major Bleeding | 131 (100.0) | 131 (97.0) | 128 (98.5) | 122 (93.1) | 131 (99.2) |
| Pairwise Comparison[a] | 0.318 | 0.184 | 0.553 | 0.010 |  |

Percentages are based on evaluable scores.
[a]P-values for comparison with warfarin, based on Cochran-Armitage test, significance for 10 mg The P-value for Dose Trend is p=0.003 for SanOrg34006, based on Cochran-Armitage test.

TABLE 5

Analysis of All Bleeding Events During Randomized Treatment; All Patients With Randomized Treatment group

|  | SanOrg34006 | | | | Warfarin |
|---|---|---|---|---|---|
|  | 2.5 mg (N = 131) | 5 mg (N = 135) | 7.5 mg (N = 130) | 10 mg (N = 131) | (N = 132) |
| Outcome | n (%) | n (%) | n (%) | n (%) | n (%) |
| Any Bleeding | 3 (2.3) | 16 (11.9) | 18 (13.8) | 20 (15.3) | 11 (8.3) |
| No Bleeding | 128 (97.7) | 119 (88.1) | 112 (86.2) | 111 (84.7) | 121 (91.7) |
| Pairwise Comparison[a] | 0.029 | 0.340 | 0.155 | 0.081 |  |

Percentages are based on evaluable scores.
[a]P-values for comparison with warfarin, based on Cochran-Armitage test, significance for 2.5 mg The P-value for Dose Trend is p=0.001 for SanOrg34006, based on Cochran-Armitage test.

Conclusions

No statistically significant dose-response relationship was observed for the tested SanOrg34006 doses with respect to the primary and secondary efficacy endpoints.

No differences in efficacy were observed between warfarin and the SanOrg34006 doses tested.

Statistically significantly less bleeding events occurred in the 2.5 mg SanOrg34006 group compared to warfarin. A statistically significant dose trend was observed for the incidence of bleeding events and for major bleeding events.

The 10 mg SanOrg34006 dose group was prematurely discontinued because the stopping rule for major bleedings applied for this dose group.

All SanOrg34006 doses and warfarin were generally well tolerated in terms of adverse events (other than bleeding events), laboratory parameters, and vital signs.

Dose-proportional pharrmacokinetics were observed, and steady state had been reached in Week 12 with trough concentrations three times as high and AUC values twice as high as the corresponding values after the first administration.

Body weight and creatinine clearance showed the strongest relationship with SanOrg34006 pharmacokinetics, resulting in an increase in SanOrg34006 exposure with decreasing body weight or creatine clearance.

Bleeding events (major bleedings and all bleedings) coincided with higher exposure to SanOrg34006, predominantly associated with age and creatinine clearance in covariate analysis.

Figure 2:
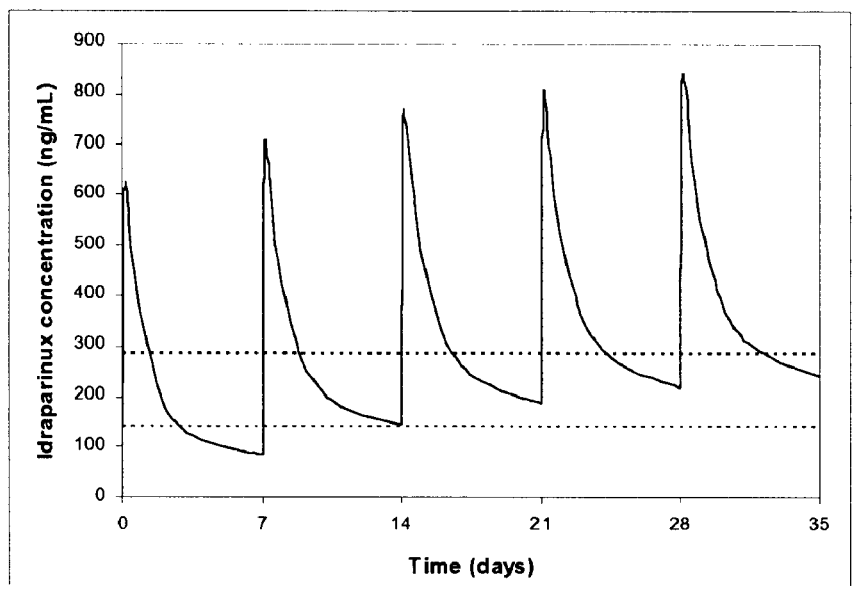
FIG. 2 is a graph of predicted average plasma concentration of SanOrg34006 (idraparinux) versus time profile during treatment of VTE patients with 2.5 mg idraparinux (once weekly).

All plasma concentrations after treatment with 2.5 mg SanOrg34006 remained below the levels associated with an increased bleeding risk Further Analysis FIG. 2 shows the predicted average plasma concentration of SanOrg34006 (idraparinux) versus time profile during treatment of VTE patients with 2.5 mg idraparinux once weekly based on results of above presented study. The range advised by ACCP [see Hyers, et al., ACCP 2001, CHEST 2001; 119:178S] is indicated between the dashed lines.

It is known that if treatment is inadequate during the week that treatment is started this has most impact on further event rates [i.e. later in time, even when accuracy has been restored (ref Brandjes et al., NEJM 1992;327 (21):1485-9)]. It is noted that the 'Brandjes' trial relates to inadequacy in acute treatment. However, inadequate treatment AFTER the acute treatment week has even a bigger impact: inadequacy over the next 12 weeks (period of the present study) can result in 25% recurrent VTE (CI Lagerstedt et al., Lancet 1985; Sep 7:515-8; R. Hull et al., NEJM 1979;301 (16):855-8).

The first SanOrg34006-week in the present study is in fact the second treatment week. Thus, if the treatment with SanOrg34006 had been inadequate early in the treatment period, incidences of deterioration of the thrombotic burden later in the treatment period might have been expected. However, even though the plasma levels of 75% of the patient population of the 2.5 mg dose group was 'too low' in terms of the ACCP guidelines, no increased deterioration was observed when compared with higher dosed populations, within the ACCP range. This is shown in Table 6 below.

TABLE 6

Incidences (%; n/N) of deterioration of overall thrombotic burden during the 12-week treatment period in different classes of observed minimal idraparinux plasma concentrations ($C_{min}$) during week 7 where data were to be collected from all randomized patients; ITT population with evaluable efficacy endpoint and appropriate PK assessment.

| $C_{min}$ class | Deterioration |
|---|---|
| <300 ng/mL | 3.1% |
| | 3/96 |
| 300-600 ng/mL | 5.4% |
| | 8/148 |
| 600-900 ng/mL | 6.3% |
| | 9/142 |
| 900-1200 ng/mL | 7.8% |
| | 4/51 |
| ≧1200 ng/mL | 4.5% |
| | 1/22 |

PK = Pharmacokinetic; the appropriate PK assessment refers to the Cmin, which is the concentration just before the next administration, also referred to as the Ctrough or trough level, the lowest level detectable for each administered subsequent dose

What is claimed is:

1. A method of for the treatment of venous thromboembolic events in a patient with deep thrombosis which comprises parenterally administering once a week to said patient a dose of 2.5 mg of the pentasaccharide methyl O-(2,3,4-tri-O-methyl-6-O-sulfo-α-D-glucopyranosyl)-(1→4)-O-(2,3-di-O-methyl-β-D-glucopyranosyl uronic acid)-(1→4)-O-(2,3,6-tri-O-sulfo-α-D-glucopyranosyl)-(1→4)-O-(2,3-di-O-methyl-α-L-idopyranosyl uronic acid)-(1→4)-2,3,6-tri-O-sulfo-α-D-glucopyranoside or a pharmaceutically acceptable salt thereof.

2. A method according to claim 1, wherein the pentasaccharide is in the form of its nonasodium salt (SanOrg 34006).

* * * * *

UNITED STATES PATENT AND TRADEMARK OFFICE
CERTIFICATE OF CORRECTION

| | | |
|---|---|---|
| PATENT NO. | : 7,709,463 B2 | Page 1 of 1 |
| APPLICATION NO. | : 10/502706 | |
| DATED | : May 4, 2010 | |
| INVENTOR(S) | : Ronald Gijsbertus Maria Van Amsterdam | |

It is certified that error appears in the above-identified patent and that said Letters Patent is hereby corrected as shown below:

On the cover page, item (54), in column 1, in "Title", line 2, after "VENOUS" insert -- THROMBOEMBOLIC --.

In column 1, line 2, after "VENOUS" insert -- THROMBOEMBOLIC --.

In column 1, line 21, delete "(wafarin" and insert -- (warfarin --, therefor.

In column 1, line 60, delete "plasia" and insert -- plasma --, therefor.

In column 7, line 28, delete "creatine" and insert -- creatinine --, therefor.

In column 8, line 37, in claim 1, after "method" delete "of".

In column 8, line 38, in claim 1, after "deep" insert -- venous --.

In column 8, line 47, in claim 2, delete "A" and insert -- The --, therefor.

Signed and Sealed this
Fifth Day of April, 2011

David J. Kappos
*Director of the United States Patent and Trademark Office*